US011542552B2

(12) United States Patent
Lee et al.

(10) Patent No.: US 11,542,552 B2
(45) Date of Patent: Jan. 3, 2023

(54) FABRICATION OF NANOCHANNEL WITH INTEGRATED ELECTRODES FOR DNA SEQUENCING USING TUNNELING CURRENT

(71) Applicant: SEAGATE TECHNOLOGY LLC, Fremont, CA (US)

(72) Inventors: Kim Yang Lee, Fremont, CA (US); Thomas Young Chang, Menlo Park, CA (US); David S. Kuo, Palo Alto, CA (US); ShuaiGang Xiao, Fremont, CA (US); Xiaomin Yang, Livermore, CA (US); Koichi Wago, Sunnyvale, CA (US)

(73) Assignee: SEAGATE TECHNOLOGY LLC, Fremont, CA (US)

( * ) Notice: Subject to any disclaimer, the term of this patent is extended or adjusted under 35 U.S.C. 154(b) by 387 days.

(21) Appl. No.: 16/909,827

(22) Filed: Jun. 23, 2020

(65) Prior Publication Data
US 2020/0377939 A1 Dec. 3, 2020

Related U.S. Application Data

(62) Division of application No. 15/886,511, filed on Feb. 1, 2018, now Pat. No. 10,731,210.
(Continued)

(51) Int. Cl.
*B81C 1/00* (2006.01)
*B01L 3/00* (2006.01)
(Continued)

(52) U.S. Cl.
CPC ...... *C12Q 1/6869* (2013.01); *B01L 3/502707* (2013.01); *B81C 1/00071* (2013.01);
(Continued)

(58) Field of Classification Search
None
See application file for complete search history.

(56) References Cited

U.S. PATENT DOCUMENTS 5,007,984 A 4/1991 Tsutsumi et al.
5,071,714 A 12/1991 Rodbell et al.
(Continued)

FOREIGN PATENT DOCUMENTS

WO 2004077503 A3 3/2005
WO 2015042200 A1 3/2015
(Continued)

OTHER PUBLICATIONS

Ohshiro, Takahito et al., "Single-Molecule Tunnel-Current Based Identification of DNA/RNA Towards Sequencing by Using Nano-MDBJ," 16th International Conference on Miniaturized Systems for Chemistry and Life Sciences, pp. 204-206, Oct. 28-Nov. 1, 2012.
(Continued)

*Primary Examiner* — Robert T. Crow
(74) *Attorney, Agent, or Firm* — Holzer Patel Drennan

(57) ABSTRACT

A DNA sequencing device and related methods, wherein the device includes a substrate, a nanochannel formed in the substrate, a first electrode positioned on a first side of the nanochannel, and a second electrode. The second electrode is positioned on a second side of the nanochannel opposite the first electrode and is spaced apart from the first electrode to form an electrode gap that is exposed in the nanochannel. At least a portion of first electrode is movable relative to the second electrode to decrease a size of the electrode gap.

9 Claims, 16 Drawing Sheets

Related U.S. Application Data

(60) Provisional application No. 62/453,298, filed on Feb. 1, 2017.

(51) Int. Cl.
  *G01N 27/327* (2006.01)
  *C12Q 1/6869* (2018.01)
  *G01N 27/447* (2006.01)

(52) U.S. Cl.
  CPC ....... *G01N 27/3278* (2013.01); *G01N 27/447* (2013.01); *B01L 2300/0645* (2013.01); *B01L 2300/0816* (2013.01); *B01L 2300/0887* (2013.01); *B01L 2300/0896* (2013.01); *B81B 2201/032* (2013.01); *B81B 2201/058* (2013.01); *B81B 2203/0109* (2013.01); *G01N 27/44791* (2013.01)

(56) References Cited

U.S. PATENT DOCUMENTS

| | | |
|---|---|---|
| 5,127,989 A | 7/1992 | Haraguchi et al. |
| 6,627,067 B1 | 9/2003 | Branton et al. |
| 7,416,993 B2 | 8/2008 | Segal et al. |
| 7,582,490 B2 | 9/2009 | Golovchenko et al. |
| 8,105,471 B1 | 1/2012 | Han et al. |
| 8,901,621 B1 | 12/2014 | Bai et al. |
| 9,410,923 B2 | 8/2016 | Sauer et al. |
| 10,247,700 B2 | 4/2019 | Hu et al. |
| 10,261,066 B2 | 4/2019 | Ikeda |
| 10,413,903 B2 | 9/2019 | Taniguchi |
| 10,712,334 B2 | 7/2020 | Choi et al. |
| 2002/0039737 A1 | 4/2002 | Chan et al. |
| 2002/0081744 A1 | 6/2002 | Chan et al. |
| 2003/0040173 A1* | 2/2003 | Fonash ............ B01J 19/0093 438/622 |
| 2003/0111440 A1 | 6/2003 | Roitman et al. |
| 2003/0141189 A1 | 7/2003 | Lee et al. |
| 2006/0246497 A1 | 11/2006 | Huang et al. |
| 2008/0171316 A1 | 7/2008 | Golovchenko et al. |
| 2010/0188109 A1 | 7/2010 | Edel |
| 2010/0267158 A1 | 10/2010 | Chou et al. |
| 2011/0120868 A1 | 5/2011 | Lindsay et al. |
| 2011/0174629 A1 | 7/2011 | Bouchet et al. |
| 2011/0224098 A1 | 9/2011 | Luan et al. |
| 2012/0037919 A1 | 2/2012 | Xu et al. |
| 2012/0325664 A1 | 12/2012 | Shim et al. |
| 2012/0326732 A1 | 12/2012 | Cho et al. |
| 2013/0256013 A1 | 10/2013 | Siman et al. |
| 2013/0334047 A1 | 12/2013 | Jeong et al. |
| 2014/0008225 A1 | 1/2014 | Jeon et al. |
| 2014/0045270 A1 | 2/2014 | Shim et al. |
| 2014/0151228 A1 | 6/2014 | Royyuru et al. |
| 2014/0312002 A1 | 10/2014 | Peng |
| 2014/0326954 A1 | 11/2014 | Han et al. |
| 2016/0153105 A1 | 6/2016 | Gumbercht |
| 2016/0319342 A1 | 11/2016 | Kawai et al. |
| 2017/0144158 A1 | 5/2017 | Taniguchi |
| 2017/0146510 A1 | 5/2017 | Ikeda et al. |
| 2017/0253479 A1 | 9/2017 | Nikoobakht, IV |
| 2018/0120287 A1 | 5/2018 | Henck |
| 2019/0310200 A1 | 10/2019 | Lee et al. |

FOREIGN PATENT DOCUMENTS

| | | |
|---|---|---|
| WO | 2015057870 A1 | 4/2015 |
| WO | 2015170782 A1 | 11/2015 |

OTHER PUBLICATIONS

Iqbal, Samir M., et al., Nanopores, Springer, New York, US, 2011.

Di Ventra, Massimiliano, et al., "Decoding DNA, RNA and peptides with quantum tunneling," Nature Nanotechnology, vol. 11, Feb. 2016, pp. 117-126.

Feng, Yanxiao, et al., "Nanopore-based Fourth-generation DNA Sequencing Technology," Genomics Proteomics Bioinformatics, 13 (2015), pp. 4-16.

Ivanov, A.P., et al., "DNA Tunneling Detector Embedded in a Nanopore," Nano Letters, 2011, 11, pp. 279-285.

Ke, Rongqin, et al., "Fourth Generation of Next-Generation Sequencing Technologies: Promise and Consequences," Human Mutation, vol. 37, No. 12, 2016, pp. 1363-1367.

Kulski, Jerzy K., "Next-Generation Sequencing—An Overview of the History, Tools, and 'Omic' Applications," http://dx.doi.org/10.5772/61964, 2015, 59 pages.

Duan et al., "Review article: Fabrication of nanofluidic devices," Biomicrofluidics 7, 026501 (2013).

Ohshiro et al., "Single=Molecule Electrical Random Resequencing of DNA and RNA," Scientific Reports, 2: 501, 1-7, Jul. 10, 2012.

Carson et al., "Challenges in DNA motion control and sequence readout using nanopore devices," Nanotechnology, 26(7), pp. 1-24, Jan. 2016.

Ohshiro et al., "Complemetary base-pair-facilitated electron tunneling for electrically pinpointing complementary nucleobases," PNAS, 103(1), 10-14, Jan. 2006.

Heerema et al., "Graphene nanodevices for DNA sequencing," Nature Nanotechnology, 11, 127-136, Feb. 2016.

Alvarez et al., "DNA/RNA transverse current sequencing: intrinsic structural noise from neighboring bases," Frontiers in Genetics, 6 (213), 1-11, Jun. 2015.

\* cited by examiner

FABRICATION OF NANOCHANNEL WITH INTEGRATED ELECTRODES FOR DNA SEQUENCING USING TUNNELING CURRENT

RELATED APPLICATIONS

This application is a divisional application of U.S. patent application Ser. No. 15/886,511 filed Feb. 1, 2018, now U.S. Pat. No. 10,731,210, which claims the benefit of the filing date of U.S. Provisional Application No. 62/453,298, filed on Feb. 1, 2017, and entitled FABRICATION OF NANOCHANNEL WITH INTEGRATED ELECTRODES FOR DNA SEQUENCING USING TUNNELING CURRENT, the disclosures of which are incorporated in their entirety by this reference.

SUMMARY

One aspect of the present disclosure relates to DNA sequencing devices and related methods for fabricating a device for single-molecule DNA detection and sequencing. One aspect of the present disclosure relates to a DNA sequencing device, which includes a substrate, a nanochannel formed in the substrate, a first electrode positioned on a first side of the nanochannel, and a second electrode. The second electrode is positioned on a second side of the nanochannel opposite the first electrode, and is spaced apart from the first electrode to form an electrode gap that is exposed in the nanochannel. At least a portion of the first electrode is movable relative to the second electrode to decrease a size of the electrode gap.

The first electrode has opposing ends and a middle portion. The ends may be fixed relative to the second electrode, and the middle portion may be movable relative to the second electrode. The electrode gap may be no more than about 2 nm. The first electrode may be arranged parallel with the length dimension of the nanochannel, and the second electrode may be arranged perpendicular to the length dimension of the nanochannel. The first electrode may be arranged parallel with the nanochannel and the second electrode may be arranged perpendicular to the top electrode. The device may also include an actuator, which is operable to move the portion of the first electrode. The actuator may include one of a heating element, a piezoelectric or piezo ceramic material, a cooling element, and an electrostatic member. The device may include a position stop arranged to limit an amount of movement of the first electrode relative to the second electrode. The device may include a hydrophobic surface feature positioned in the nanochannel.

Another aspect of the present disclosure relates to a method of forming a nanochannel device for DNA sequencing. The method includes forming a channel in a substrate, depositing a first electrode material in the channel to form a first electrode, depositing a carbon or $SiO_2$ layer on the substrate, depositing a second electrode layer on the carbon or $SiO_2$ layer, and forming a pair of first trenches in the second electrode layer to form a second electrode. The method also includes forming the first trenches into the carbon or $SiO_2$ layer to expose the first electrode, removing a portion of the carbon or $SiO_2$ layer positioned between the first and second electrodes, a portion of the first electrode being movable relative to the second electrode to vary a spacing between the first and second electrodes, and depositing a filler material on the second electrode layer and into the first trenches. The nanochannel may be defined in part between the first and second electrodes and the filler material positioned in the first trenches.

The method may also provide for forming the first trenches in the second electrode layer by trench patterning using at least one of deep ultraviolet (DUV) lithography, 193 nm lithography, e-beam lithography, and nanoimprint lithography (NIL). The filler material may be at least one of a photoresist material and an insulation material. The method may include, prior to forming the channel in the substrate, coating the substrate to form a first layer, forming a trench in the first layer, etching the channel in the substrate through the trench, and stripping the first layer from the substrate after depositing the first electrode material in the channel and before depositing the carbon or $SiO_2$ layer on the substrate.

The method may include depositing the first electrode material on the first layer when depositing the first electrode material in the channel. The method may include, before forming the first trenches in the second electrode layer, forming a third photoresist layer on the second electrode layer, and forming the first trenches in the third photoresist layer. Forming the third photoresist layer may include spinning material of the third photoresist layer on the second electrode layer. Forming the first trenches in the carbon or $SiO_2$ layer and removing the portion of the carbon or $SiO_2$ layer may include using high pressure O2 reactive ion etching (RIE) or wet etching. The spacing between the first and second electrodes may be adjustable to be in the range of about 0.3 nm to about 2 nm.

A further aspect of the present disclosure relates to a method of DNA sequencing. The method includes providing a DNA sequencing device having a nanochannel and first and second electrodes, a spacing between the first and second electrodes defining an electrode gap, the electrode gap being exposed in the nanochannel, moving a portion of the first electrode to adjust a size of the electrode gap, passing a DNA strand through the electrode gap, and detecting a change in electronic signal as the DNA strand passes through the electrode gap. The size of the electrode gap may be adjusted to be in the range of about 0.3 nm to about 2 nm. The detected change in electronic signal may be associated with one or more individual nucleotides of the DNA strand. The change in electronic signal may be used to determine a sequence of the nucleotides for the DNA strand.

The foregoing has outlined rather broadly the features and technical advantages of examples according to this disclosure so that the following detailed description may be better understood. Additional features and advantages will be described below. The conception and specific examples disclosed may be readily utilized as a basis for modifying or designing other structures for carrying out the same purposes of the present disclosure. Such equivalent constructions do not depart from the scope of the appended claims. Characteristics of the concepts disclosed herein, including their organization and method of operation, together with associated advantages will be better understood from the following description when considered in connection with the accompanying figures. Each of the figures is provided for the purpose of illustration and description only, and not as a definition of the limits of the claims.

BRIEF DESCRIPTION OF THE DRAWINGS

A further understanding of the nature and advantages of the present disclosure may be realized by reference to the following drawings. In the appended figures, similar components or features may have the same reference label.

Further, various components of the same type may be distinguished by following a first reference label with a dash and a second label that may distinguish among the similar components. However, features discussed for various components, including those having a dash and a second reference label, apply to other similar components. If only the first reference label is used in the specification, the description is applicable to any one of the similar components having the same first reference label irrespective of the second reference label.

DETAILED DESCRIPTION

Figure 1:
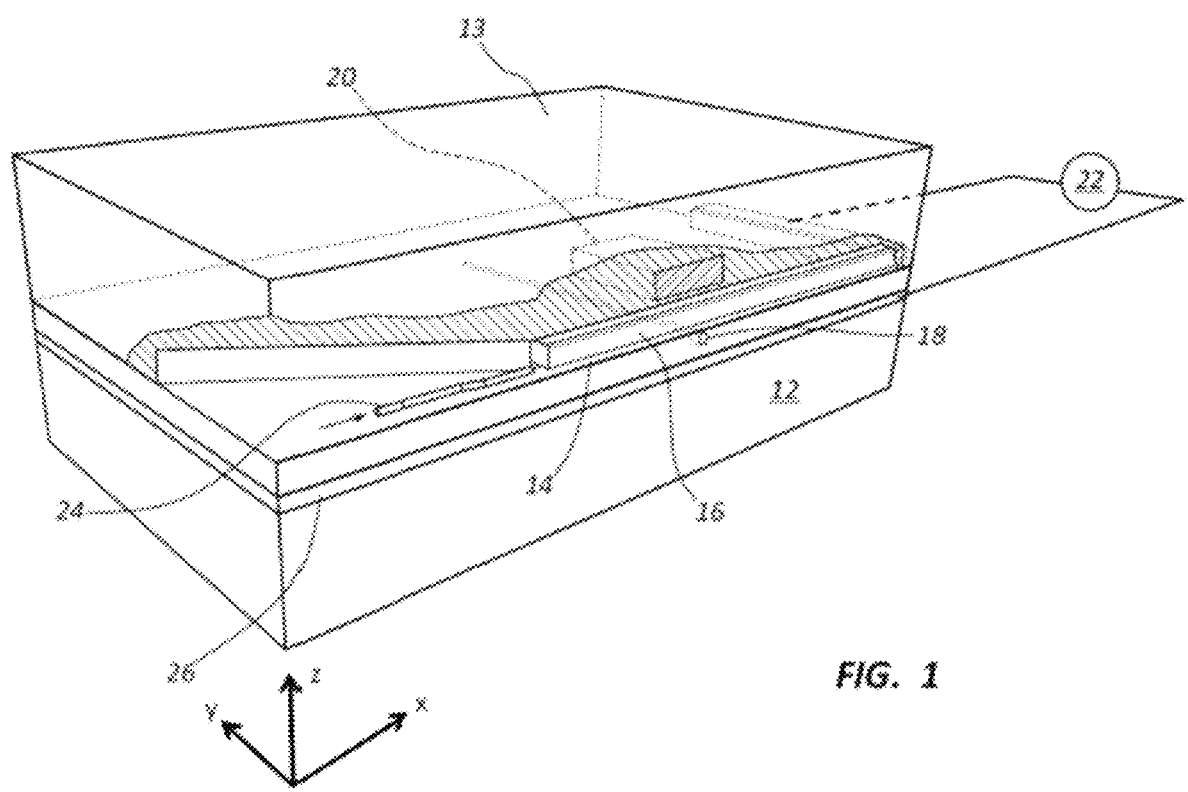
FIG. 1 is a schematic perspective view of DNA sequencing device in accordance with the present disclosure.

Despite considerable efforts, DNA sequencing today still suffers from high costs and low speeds. To address all these issues, various methods have been proposed over the past decade that would allow individual DNA strands to be read directly. Among these, nanopore and nanochannel based approaches have emerged as the most promising. However, many challenges exist related to fabricating a channel and/or pore opening that is sufficiently small to limit passage to a single DNA strand, and there is no such report of a relatively mature method that address this unmet need.

Direct DNA sequencing has drawn attention due to its advantages on long read length, high throughput and low cost. Direct DNA sequencing methods using transverse tunneling current measurement have been studied extensively in literature. However, a manufacturably viable direct DNA sequencing device with required dimensions for the gap between the nanoelectrodes, nor methods for creating such a device, have not been discovered. Conventional MEMS and nanofabrication methods are inadequate for creating the required structure.

The present disclosure generally relates to DNA sequencing, and more particularly relates to DNA sequencing devices having nanochannels and nanoelectrodes, and related methods of fabricating such devices. The present disclosure may also relate to DNA sequencing using such devices. The present disclosure further relates to methods for fabricating a device for single-molecule DNA detection and sequencing. The device may include a nanofluidic channel through which DNA strands can be guided through a sub-nanometer electrode gap.

The disclosed DNA sequencing devices may be designed to be portable and to provide data sequence in real time. Also disclosed here are DNA sequencing devices that are configured to read DNA using tunneling current and based on ionic current measurement through a sub-nanometer orifice, which is expected to be faster and more accurate than existing products and methods.

Direct measure of individual bases of long DNA strands rapidly and with low cost is one goal of DNA sequencing. Among these options, nanopore- and nanochannel-based approaches that measure a transverse signal across individual bases have emerged as a promising approach. The general approach involves electrically driving DNA and RNA strands through a nanopore or narrow channel via ionic flow or driven by a pressure gradient. As the strand passes a high resolution sensor embedded inside the channel, the high spatial resolution sensor measures the unique properties of the individual bases (A,T,C,G). One type of sensor would consist of a conductive electrode or electrode pair that measures the unique tunneling currents associated with the base, thereby identifying and resolving the four unique base types.

However, there are several significant challenges associated with the fabrication of such devices at low cost that can spatially resolve individual bases of each strand, wherein the bases are on the order of about 1 nm in size in a transverse direction. One challenge is the ability to fabricate a channel width on the order of about 1 nm with accuracy and repeatability to obtain tunneling current that is exponential verse distance. For example, the signal tunneling current would reduce by a factor of about 1000× if spacing is increased between probe and base molecule by only about 0.5 nm. A second challenge relates to fabrication of a sensor that is 1 nm or less in width in order to resolve and detect individual bases (e.g., A,T,C,G) in the DNA strand.

One method to form and maintain a channel opening with Angstrom level size control is to actively set the channel opening using mechanical actuation. The actuation may move an electrode member that is exposed within the channel to alter the channel opening through which the DNA strand passes. Achieving actuation to change the electrode and grounding distance may involve anchoring two ends of the channel while the center section that is being actuated is surrounded by highly compliant material. The portion of the channel that is movable may be formed of a conductive material and act as an electrode member. The use of compliant material may permit deformation of the side wall structure and enable a change in the electrode to ground distance. Although, it is possible to find a highly compliant material, the best approach may be to not embed the channel in any material at all, but rather provide a portion of the structure free standing in ambient air. Then the challenge is to fabricate a nanochannel structure that will confine the solution without having a fully enclosed physical wall structure.

The present disclosure may provide a structure and related methods that enable liquid and/or solution confinement within the channel without requiring a fully enclosed physical channel structure with four walls. Top and bottom surfaces of the channel may comprise a hydrophilic material such that liquid solution (e.g., saline solution) will flow along the channel and be confined in the channel due to capillary action (see FIGS. 4A-4C and/or FIGS. 5A-5C).

Figure 3A:
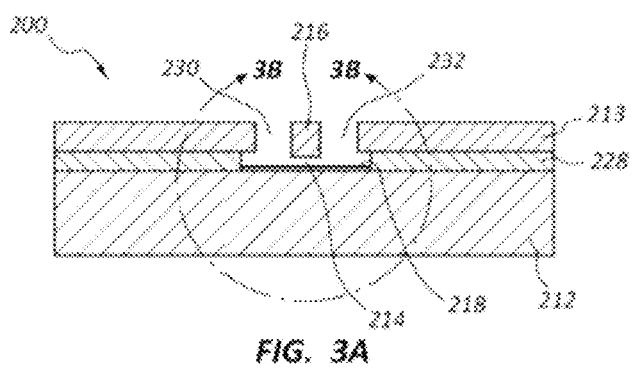
FIGS. 3A, 3B and 3C are schematic end views of an example DNA sequencing device having a hard stop layer.
Figure 3B:
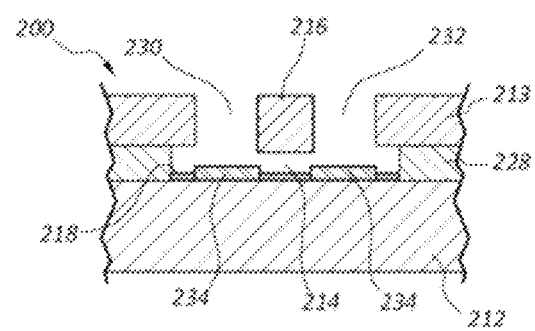
Figure 3C:
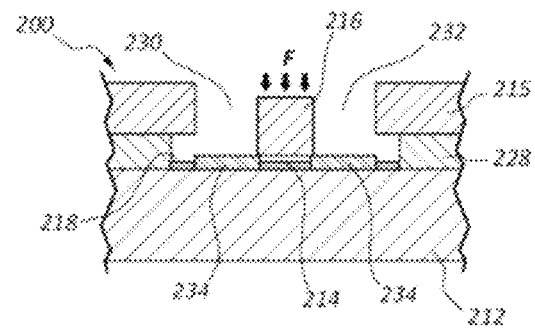

In one embodiment, thin side structures for the channel are formed using a self-aligned deposition process, which results in a physical stop to limit and maintain a minimum spacing or gap G when the actuation is turned ON (see FIGS. 3A-3C). It may be possible for no side structure to be used as the liquid can be maintained within the channel strictly by capillary action (see FIGS. 4A-4C).

Figure 5A:
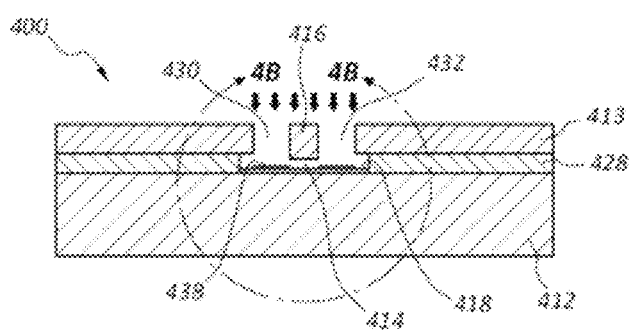
FIGS. 5A, 5B and 5C are schematic end views of an example DNA sequencing device having fluid confinement by capillary force and hydrophobic surfaces.
Figure 5B:
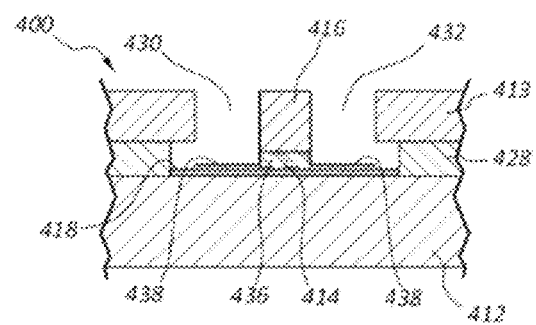
Figure 5C:
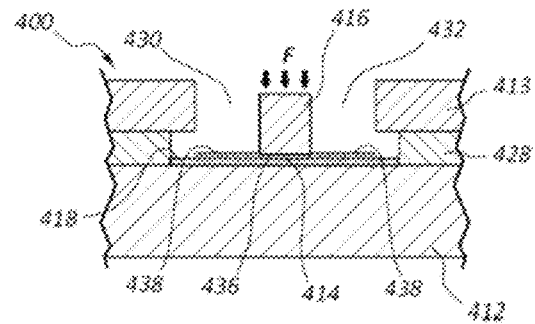

A hydrophobic coating may be used in the side region using a self-aligned deposition process combined with capillary action that would further enhance the confinement within the channel structure without the need for physical containment (see FIGS. 5A-5C).

Referring to FIG. 1, an example of DNA sequencing device 10 is shown schematically in a perspective, cut-away view. The DNA sequencing device 10 includes a substrate 12, an upper layer 13, a nanochannel 14, first and second electrodes 16, 18, an actuator 20, and a controller and/or pre-amp 22. The DNA sequencing device 10 defines a gap G between the first and second electrodes 16, 18 within the nanochannel 14 (see also FIGS. 2A and 2B). A tunneling current is measured between the first and second electrodes 16, 18 as the DNA strand 24 passes through the gap G. The size of the gap G may be modified by operating the actuator 20. The actuator 20 may move a portion of the first electrode 16 relative to the second electrode 18.

In one example, the actuator 20 comprises a heating element such as a resistive element, which generates heat when activated. The heat generated by actuator 20 expands the material of upper layer 13 in the area around the actuator 20 to move a portion of the first electrode 16 relative to the second electrode 18. In some embodiments, the actuator 20 is activated to move the first electrode 16 into contact with the second electrode 18, and then the actuator 20 is backed off or deactivated a certain amount in order to create the gap G of a desired size. In other embodiments, the actuator 20 is activated until the first electrode 16 moves a desired distance from a rest state to a final or activated state or position relative to the second electrode 18 to create the desired sized gap G.

The first electrode 16 may be fixed at opposite ends and a middle portion along the length of the first electrode 16 is movable to adjust the size of gap G. In other embodiments, one end of the electrode 16 is fixed while the opposite end is free floating thereby creating a cantilever-type arrangement for the first electrode 16. The first electrode 16 may be referred to as a top electrode and may be defined as a suspended structure. The second electrode 18, which may be referred to as a bottom electrode, may be fixed or stationary.

The first and second electrodes 16, 18 may have various sizes, shapes, and orientations. In one example (e.g., see FIG. 1), the first electrode 16 has an elongate shape with a generally rectangular cross-sectional shape. Other embodiments for the first electrode 16 may include a flat plate, an elongate member having a rounded or pointed bottom surface or downward facing structure, or other desired shape and/or size. The second electrode 18 may have an elongate shape as shown in FIG. 1. In other embodiments, the second electrode 18 may include a relatively thin, pointed, or tapered top surface that is arranged facing the first electrode 16. In other embodiments, the second electrode 18 has a generally flat or planar, plate-like structure (e.g., a layer on top of substrate 12). Forming the first and second electrodes 16, 18 in a way that the portions of the first and second electrodes 16, 18 that are closest to each other have a relatively small surface area (e.g., a line or point) may provide for improved signal to noise ratio (SNR) when measuring the tunneling current as the DNA strand passes through the gap G.

As discussed above, the gap G is typically in the range of about 0.3 nm to about 2 nm when in a final, adjusted position ready for measuring tunneling current associated with the DNA strand. The gap G may be closer in size to the height or spacing of a nanochannel 14 when the electrodes 16, 18 are in a rest or unadjusted position (i.e., when the actuator 20 is in an OFF state). The gap G in the rest or unactuated position for the electrodes may be in the range of about 2 to about 20 nm, and more particularly about 5 nm to about 10 nm.

Many other types of actuating devices and technology may be used for the actuator 20. In one example, the actuator 20 includes a piezoceramic or piezoelectric material. In another example, the actuator 20 includes an electrostatic material. In a yet further example, the actuator 20 generates a magnetic field or force. In a still further example, the actuator 20 includes a cooling element that causes constriction of the material of upper layer 13. In the cooling element embodiment, the first and second electrodes 16, 18 are typically arranged in contact with each other when in a rest state, and actuating the cooling element of the actuator 20 moves the first and second electrodes 16, 18 apart as the material of upper layer 13 contracts in size.

The DNA sequencing device 10 may also include a heat shield 26. The heat shield 26 may be positioned between the actuator 20 and the first electrode 16. The heat shield 26 may limit potential heat-related damage to the first electrode 16 and/or the DNA strand 24 as it passes through the nanochannel 14. Typically, the heat shield 26 comprises a heat conductive material.

The first and second electrodes 16, 18 are shown in FIG. 1 in a perpendicular arrangement relative to each other. Other embodiments are possible in which the first and second electrodes 16, 18 have other orientations such as, for example, being parallel with each other. Further, the first and second electrodes 16, 18 may be aligned in parallel with the nanochannel 14 or arranged at an angle relative to the nanochannel 14. In at least one alternative embodiment, the second electrode is arranged in parallel with the nanochannel 14 and may be in the form of a plate or layer that is exposed along an entire length of the nanochannel 14, and the first electrode 16 is arranged perpendicular to the nanochannel 14. In a still further embodiment, the first and second electrodes 16, 18 may be arranged end-to-end with the exposed ends of the first and second electrodes 16, 18 being positioned within the nanochannel 14. Actuation of the actuator 20 may move one or both of the first and second electrodes 16, 18 longitudinally relative to each other to modify the size of gap G.

In operation, a fluid may be driven through the nanochannel 14 using, for example, an electrophoretic field along the length of the nanochannel 14. A DNA strand 24 may be carried by the moving fluid through the nanochannel 14. A DNA strand transiting through the gap G between the top and bottom electrodes 16, 18 may be sequenced by measuring a tunneling current passing through the nucleotides of the DNA strand 24 as each individual nucleotide passes through the gap G. Measuring the tunneling current is typically most effective when the tunneling gap G is about 1 nm or less.

Figure 2A:
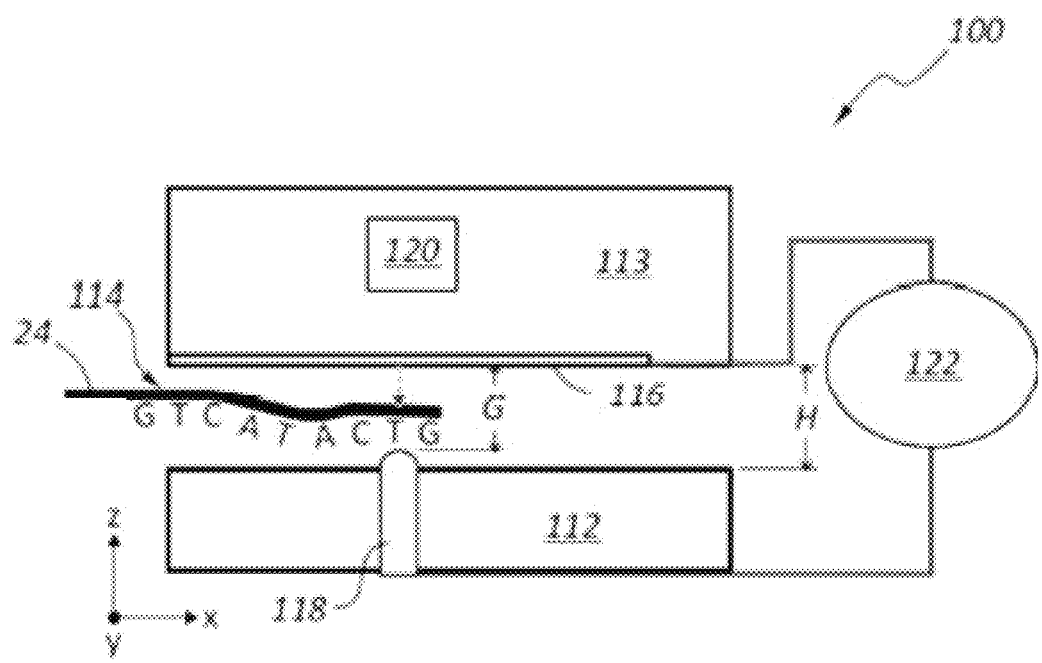
FIG. 2A is a schematic side view of a DNA sequencing device in an OFF state in accordance with the present disclosure.
Figure 2B:
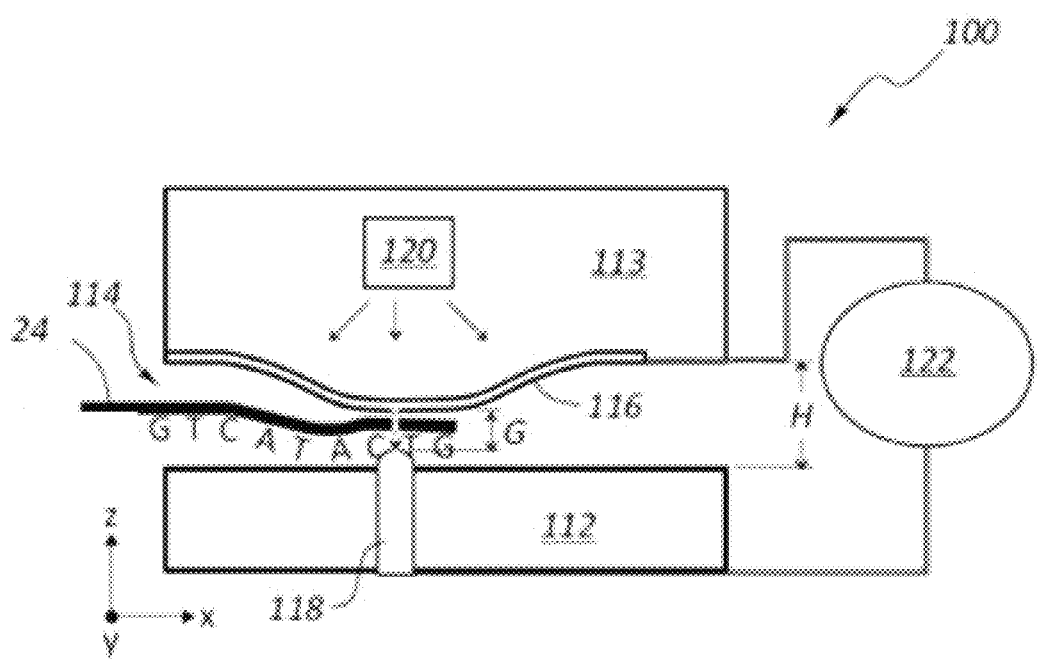
FIG. 2B is a schematic side view of the DNA sequencing device of FIG. 2A in an ON state.

FIGS. 2A and 2B schematically illustrate another example DNA sequencing device 100 as schematic side views taken along the length of a nanochannel 114. The DNA sequencing device 100 includes a substrate 112, an upper layer 113, a nanochannel 114, first and second electrodes 116, 118, an actuator 120, and a controller or pre-amp 122. FIG. 2A shows the DNA sequencing device 100 in an OFF or unactuated state for the actuator 120. The space between the first and second electrodes 116, 118 has a gap G size that is similar in size to the height H of the nanochannel 114. FIG. 2B shows the actuator 120 in an ON state in which the first electrode 116 is moved toward the second electrode 118 to reduce the size of gap G. Typically, the reduced size of gap G is in the range of about 0.3 nm to about 2 nm, and more particularly about 1 nm or less. FIG. 2B shows a DNA strand 24 passing through the nanochannel 114 and the gap G between the first and second electrodes 116, 118. The electrodes 116, 118 may detect a tunneling current that is unique for each of the nucleotides (A,T,C,G) of a DNA strand 24.

As discussed above, one or both ends of the first electrode 116 may be fixed and at least a middle portion of the first electrode 116 along its length may be movable toward and away from the second electrode 118 upon activation of the actuator 120. The description below of FIGS. 7A-7R explains examples of how the DNA sequencing devices 10, 100 may be fabricated to provide the first electrode 16, 116 with a movable portion to control the size of gap G.

FIGS. 3A-3C schematically illustrate a schematic end view of a DNA sequencing device 200. The device 200 includes a suspended first electrode 216. The first electrode 216 is formed from an upper layer 213 that has a pair of parallel trenches 230, 232 formed therein. A carbon or $SiO_2$ layer 228, which is positioned between the upper layer 213 and a substrate 212, is removed in the area of the first electrode 216 to provide a nanochannel 214 between the first and second electrodes 216, 218.

FIG. 3B shows hard stop material 234 that is deposited through the trenches 230, 232 onto a surface defining the second electrode 218. FIG. 3B shows the first electrode 216 in a rest position with the nanochannel 214 having a maximum gap G size. FIG. 3C shows a force F applied to the first electrode 216 to move the first electrode 216 into contact with the hard stop material 234. The hard stop material 234 provides a minimum size for gap G. The hard stop material 234 may also provide side surfaces for the nanochannel 214 to contain the fluid and a DNA strand that passed through the nanochannel 214.

Typically, the thickness of the hard stop material 234 is substantially equal to the targeted size of gap G (i.e., in the range of about 0.3 nm to about 2 nm, and more particularly about 1 nm or less). The hard stop material may comprise a non-compressible material, and typically comprises a non-conductive material. In one example, the hard stop material comprises at least one of silicon nitride, silicon oxide or carbon.

Figure 4A:
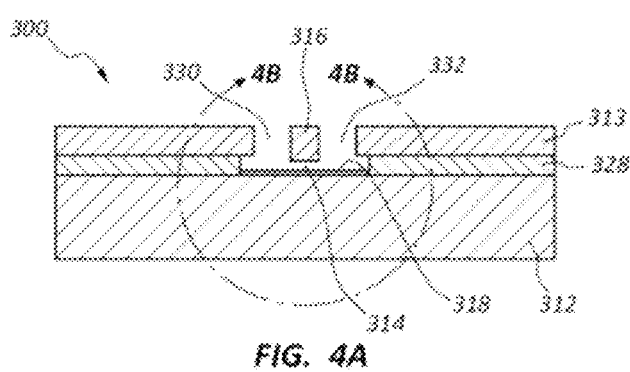
FIGS. 4A, 4B and 4C are schematic end views of an example DNA sequencing device having fluid confinement by capillary force.
Figure 4B:
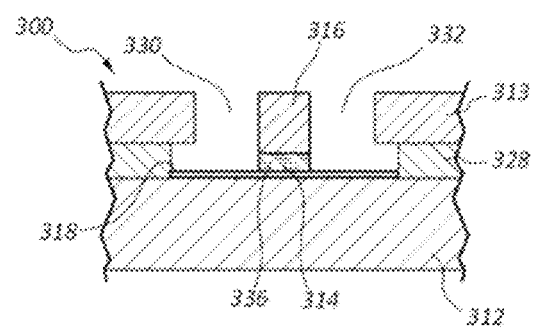
Figure 4C:
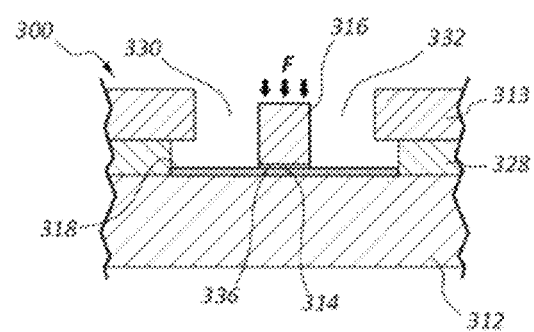

FIGS. 4A-4C schematically illustrate another example DNA sequencing device 300 as end views. FIG. 4A shows the device 300 having a suspended first electrode 316 that is defined by forming trenches 330, 332 in an upper layer 313. Portions of a carbon or $SiO_2$ layer 328 are removed in the area of the first electrode 316 to define a nanochannel 314. A second electrode 318 is positioned within or on a surface of a substrate 312 on a side of the nanochannel 314 that is opposite the first electrode 316.

FIG. 4B shows a fluid 336 confined in a nanochannel between the bottom surface of the first electrode 316 and the top surface of the substrate 312 and second electrode 318. The fluid is confined within the nanochannel 314 by capillary force. In at least some embodiments, the first and second electrodes 316, 318 and the substrate 312 comprise hydrophilic materials that promote confinement of the fluid 336 by capillary force.

FIG. 4C shows the fluid 336 confined within nanochannel 314 when a force F is applied to the first electrode 316 to move the first electrode 316 relative to the second electrode 318 to reduce the size of gap G. The size of gap G shown in FIG. 4C is typically in the range of about 0.3 nm to about 2 nm, and more preferably about 1 nm or less.

FIGS. 5A-5C illustrate an example DNA sequencing device 400 as schematic end views. The device 400 includes a substrate 412, an upper layer 413, a nanochannel 414, first and second electrodes 416, 418 and a gap G between the first and second electrodes 416, 418. The first electrode 416 is shown suspended by formation of a pair of trenches 430, 432 formed in the upper layer 413. A portion of a carbon or $SiO_2$ layer 428 is removed in the area of the first electrode 416 to create the nanochannel 414. A hydrophobic coating 438 is deposited through the trenches 430, 432 onto the second electrode 418 and substrate 412. The hydrophobic coating 438 helps contain the fluid 436 passing through the nanochannel 414, as shown in FIG. 5B. A force F applied to the first electrode 416 reduces the gap G between the first and second electrodes 416, 418, as shown in FIG. 5C. The hydrophobic coating 438 defines, at least in part, side walls of the nanochannel 414 to help contain the fluid 436. In at least some embodiments, the hydrophobic coating 438 has a thickness that is substantially equal to the desired size for gap G in the range of about 0.3 nm to about 2 nm, and more particularly about 1 nm or less. The fluid 436 may also be contained at least in part by the capillary forces promoted by, for example, materials used for formation of the first and second electrodes 416, 418, the substrate 412, and the hydrophobic material 438.

Figure 6A:
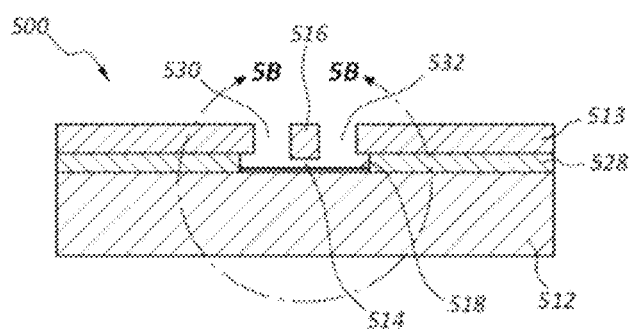
FIGS. 6A, 6B and 6C are schematic end views of an example DNA sequencing devices having a compliant stop layer.
Figure 6B:
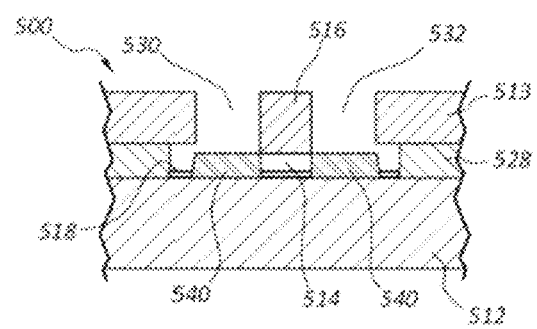
Figure 6C:
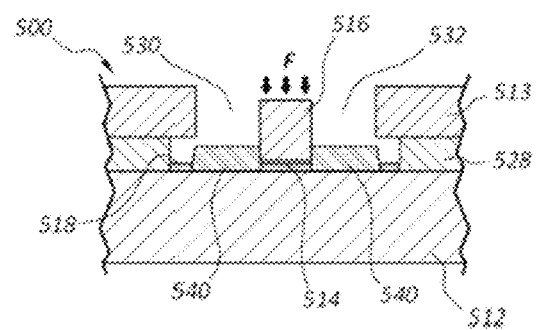

FIGS. 6A-6C schematically illustrate a DNA sequencing device 500 as end views. The device 500 includes a substrate 512, an upper layer 513, a nanochannel 514, first and second electrodes 516, 518, and a carbon or $SiO_2$ layer 528. The first electrode 516 is shown suspended by formation of trenches 530, 532 in the upper layer 513. Portions of a carbon or $SiO_2$ layer 528 are removed in the areas of the first electrode 516 to create the nanochannel 514. The second electrode 518 is positioned on a top surface of the substrate 512. A gap G is defined between the first and second electrodes 516, 518. FIG. 6B illustrates a compressible or compliant material 540 that is deposited through the trenches 530, 532 onto the substrate 512 and/or second electrode 518. The compressible material 540 may comprise a material that is elastic, compressible, or the like. Referring to FIG. 6C, when a force F is applied to the first electrode 516, the first electrode 516 contacts and at least partially compresses the compressible material 540. The compressible material 540 provides a position stop for the first electrode 516. The compressible material 540 may provide stability for the first electrode 516. The compressible material 540 may have an initial (uncompressed) thickness of about 0.5 nm to about 10 nm, and more particularly about 0.5 nm to about 5 nm. The compressible material 540 may function to help define a final or desired size for gap G to be in the range of about 0.3 nm to about 2 nm, and more particularly about 1 nm or less. The first electrode 516 may contact side surfaces of the compressible material 540 as shown in FIGS. 5B and 5C. Alternatively, the bottom surface of the first electrode 516 may contact the top surface of the compressible material 540 to more directly apply a compression force to the compressible material 540 as the force F is applied to the first electrode 516. In some embodiments, the compressible material 540 may be compressible by about 20% to about 50%.

In one example, the compressible material 540 comprises a hydrophilic material. The compressible material may be deposited by, for example, physical vapor deposition. An example compressible material is polystyrene (PS), polyethylene (PE), and Polytetrafluoroethylene (PTFE).

Figure 7A:
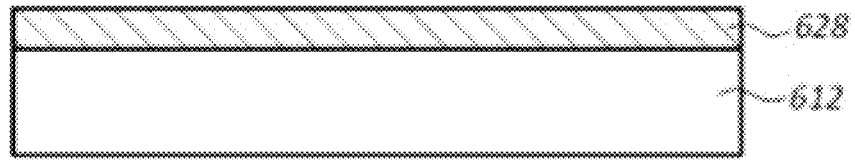
FIGS. 7A, 7B and 7C are schematic cross-sectional views showing trench fabrication steps in accordance with the present disclosure.
Figure 7B:
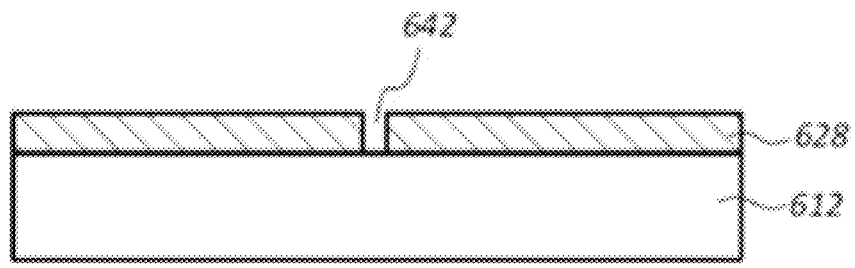
Figure 7C:
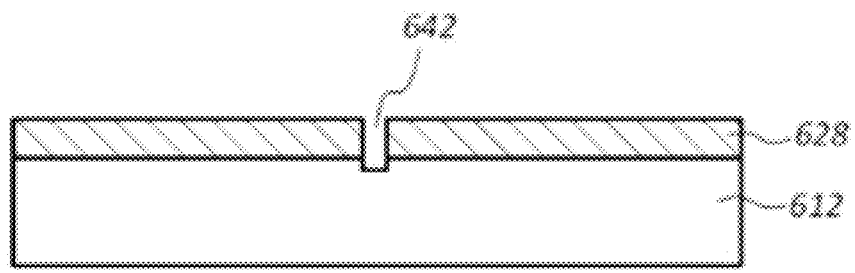
Figure 7D:
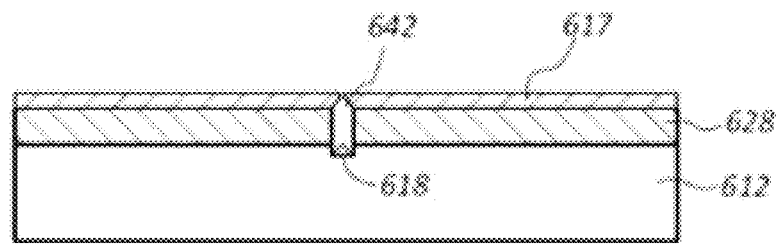
FIGS. 7D, 7E and 7F are schematic cross-sectional and plan views showing electrode fabrication steps in accordance with the present disclosure.
Figure 7E:
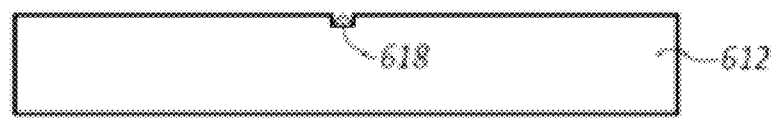
Figure 7F:
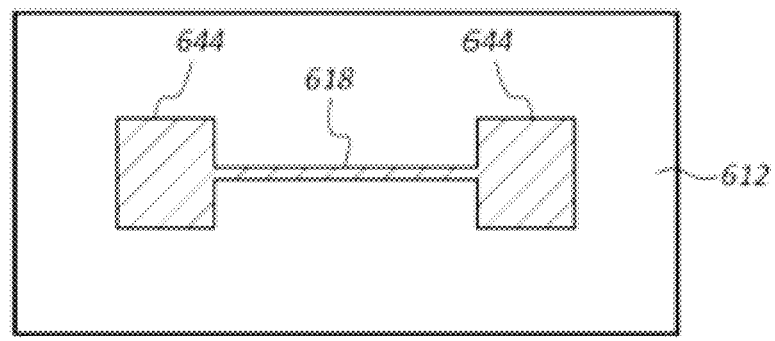
Figure 7G:
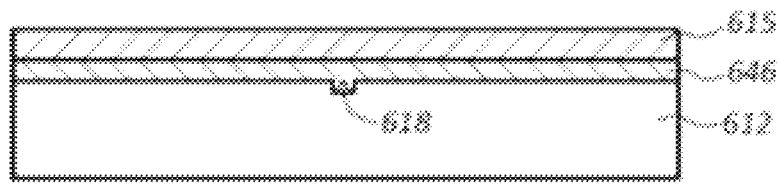
FIGS. 7G, 7H, 7I and 7J are schematic cross-sectional and plan views showing further channel fabrication steps in accordance with the present disclosure.
Figure 7H:
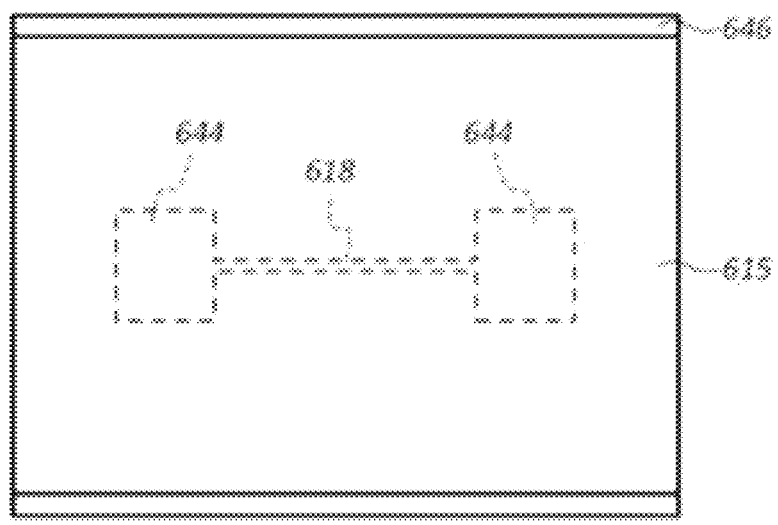
Figure 7I:
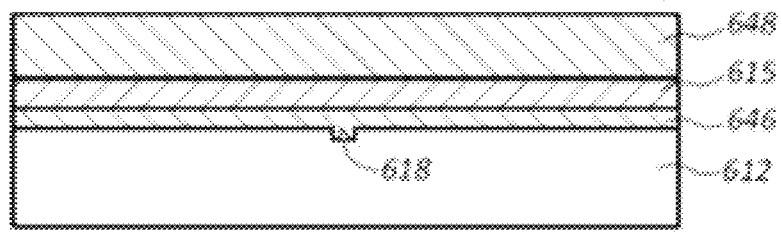
Figure 7J:
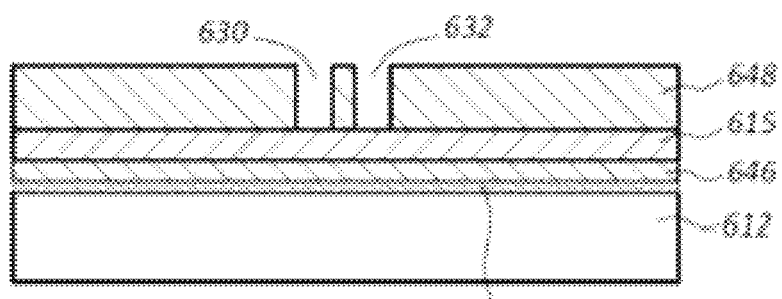
Figure 7K:
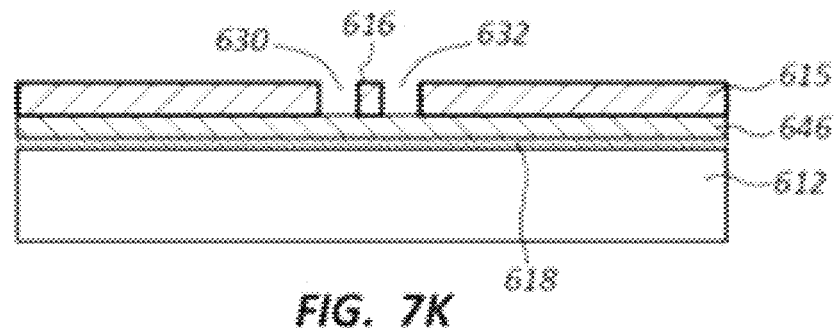
FIGS. 7K, 7L, 7M and 7N are schematic cross-sectional and plan views showing further electrode and channel fabrication steps in accordance with the present disclosure.
Figure 7L:
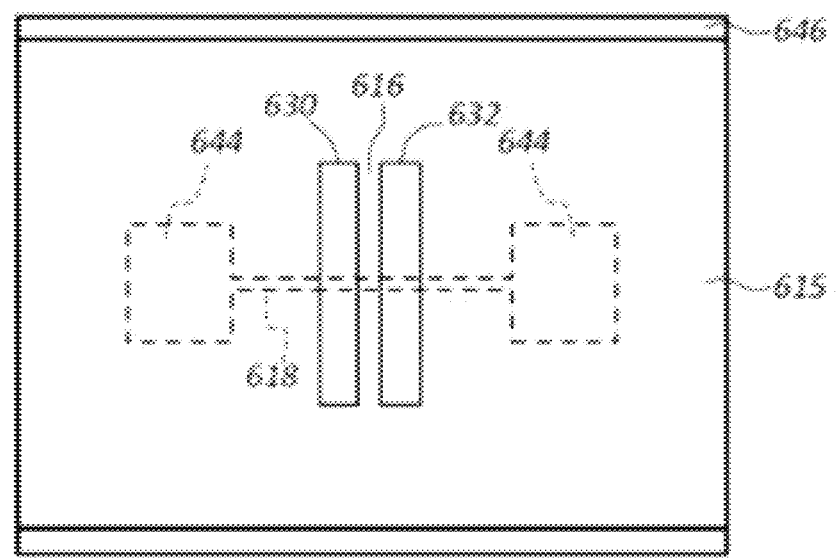
Figure 7M:
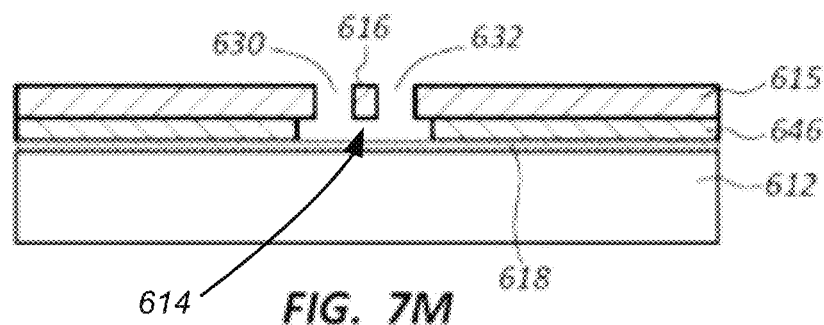
Figure 7N:
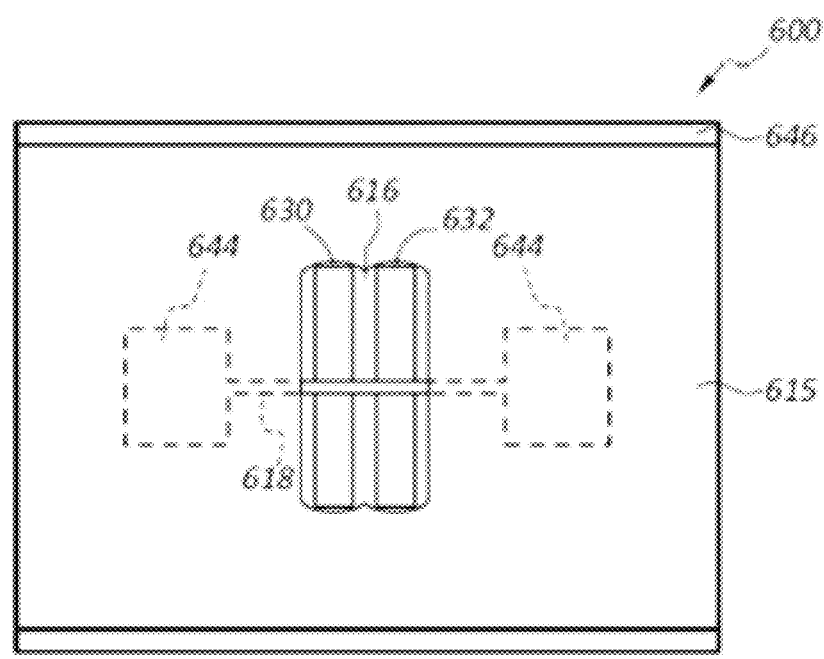
Figure 7O:
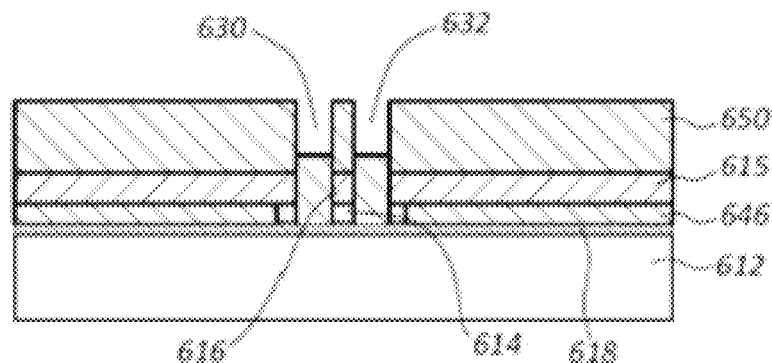
FIGS. 7O and 7P are schematic cross-sectional and plan views showing further channel fabrication steps in accordance with the present disclosure.
Figure 7P:
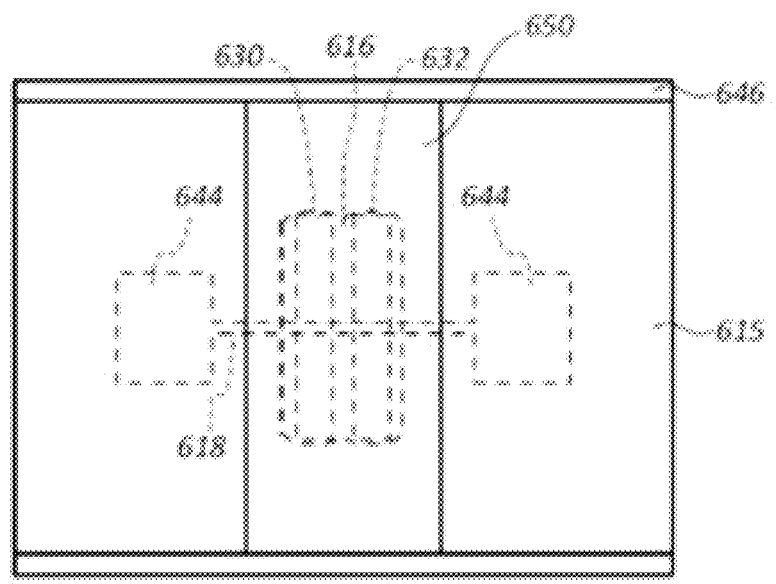
Figure 7Q:
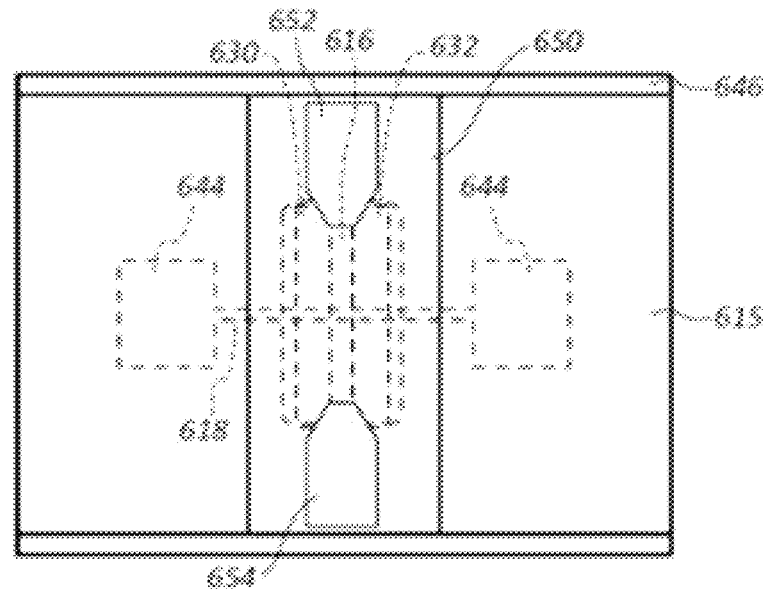
FIGS. 7Q and 7R are schematic plan views showing further fabrication steps in accordance with the present disclosure.
Figure 7R:
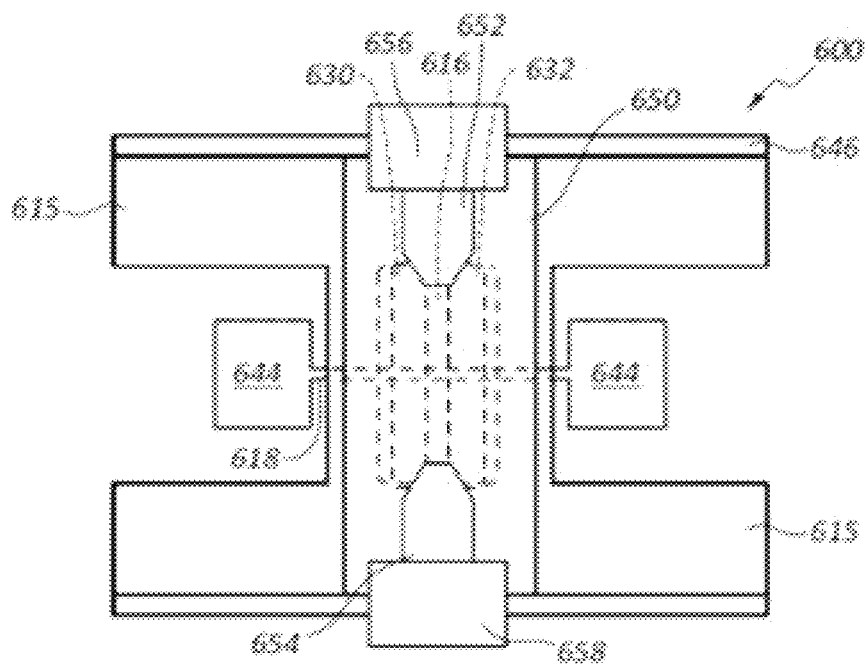

Referring now to FIGS. 7A-7R, example fabrication steps used to form DNA sequencing devices according to the present disclosure are illustrated in schematic side, cross-sectional, and/or plan views. The details disclosed with reference to FIGS. 7A-7R are explanatory only, and other materials, specifications, and processes may be used to form DNA sequencing devices with similar structures and functionality in other embodiments.

FIGS. 7A-7C illustrate steps of an example bottom tunneling electrode patterning process. FIG. 7A shows a first step of coating a resist material (ZEP) 628 on a substrate 612. The substrate 612 may comprise, for example, a silicone (Si) wafer. The resist material 628 may be coated with a thickness of about, for example, 50 nm.

FIG. 7B illustrates formation of a trench 642 in the resist material 628. In one embodiment, an electron beam lithography (EBL) method may be used to create the trench 642. The trench 642 may have a line width in the range of about, for example, 10 nm to about 15 nm. FIG. 7C illustrates the trench 642 being formed to a further depth into the substrate 612. In one example, a reactive ion etching (RIE) process may be used to etch the depth of the trench 642 into the substrate 612 (e.g., a CF4 RIE process). The depth of the trench 642 formed in the substrate 612 may be in the range of about, for example, 2 nm to about 10 nm, and more particularly about 4 nm.

FIGS. 7D-7F illustrate further steps of the example bottom tunneling electrode patterning process. FIG. 7D illustrates formation of a conductive layer (e.g., chromium (Cr)) that is deposited on the resist layer 628 and within the trench 642. The conductive layer 617 may be formed using, for example, evaporation (e.g., Denton). The conductive layer 617 may have a thickness of, for example, about 3 nm to about 10 nm, and more particularly about 5 nm. The conductive material positioned in the trench 642 may provide a tunneling electrode 618 once the resist layer 628 and conductive layer 617 are removed from the substrate 612.

FIG. 7E illustrates the layers 617, 628 removed from the substrate 612. The layer 617, 628 may be removed using, for example, a liftoff process. The electrode 618 may have a generally triangular cross-sectional shape (also referred to as a tapered or pointed shape). The electrode 618 may protrude outside of the trench 642 or may be entirely confined within the trench 642.

FIG. 7F is a plan view from above showing the electrode 618 positioned within the trench. Electrode contacts 644 may be positioned at an opposite end of the electrode 618. The electrode contacts 644 may be connected to, for example, the controller and/or pre-amp 22/122 of the example DNA sequencing devices described above.

FIGS. 7G-7J illustrate further steps of forming a nanochannel of the DNA sequencing device. FIG. 7G shows formation of a layer 646 deposited on the top surface of the substrate 612 (e.g., carbon (C) or $SiO_2$ material). A top electrode layer 615 is deposited on the layer 646. The electrode layer 615 may comprise a conductive material such as, for example, Tantalum (Ta). The layers 646, 615 may each have a thickness of about, for example, 3 nm to about 10 nm, and more particularly about 5 nm. FIG. 7H shows a top plan view of the layers 615, 646 over the substrate 612 shown in FIG. 7G.

FIG. 7I shows addition of a resist layer on top of the conductive top electrode layer 615. The resist layer 648 may comprise, for example, ZEP material. The resist layer 648 may be added using, for example, spinning techniques. The resist layer 648 may have a thickness of, for example, about 30 nm to about 60 nm.

FIG. 7J shows formation of a pair of trenches 630, 632 in the resist layer 648. In one example, the trenches 630, 632 may be formed using EBL techniques. The spacing between the trenches 630, 632 may define at least in part a width of a resultant nanochannel. Typically, the trenches 630, 632 have a width in the range of about 50 nm to about 150 nm, and more particularly about 100 nm. The resulting spacing between the trenches 630, 632 is typically in the range of about 20 nm to about 40 nm, and more particularly about 30 nm. A narrower width for the resultant spacing between the trenches 630, 632 may be possible by over-exposing the trenches 630, 632 during the EBL process. A potential advantage related to the steps shown with reference to FIGS. 7G-7J is that there may be no need for resolution push in a lithography setting.

FIGS. 7K-7N illustrate further steps of the nanochannel formation, including transferring the trench pattern of trenches 630, 632 into the layer 615. Portions of the layer 646 below the trenches 630, 632 and the strip defining electrode 616, which is the first or top electrode 616, are removed to create the nanochannel 614 as shown in FIG. 7M. FIG. 7K and 7L show end and top plan views, respectively, of the trenches 630, 632 transferred into the layer 615. FIGS. 7M and 7N show end and top plan views, respectively, of the portions of layer 646 removed to define the nanochannel 614, which also exposes a portion of the bottom or second electrode 618 within the nanochannel 614.

In one example, a high pressure $O_2$ RIE process may be used to remove the portions of layer 646. The portions of layer 646 underneath the electrode 616 may be removed completely by undercutting. In one example, wet etching may be employed to remove the portions of layer 646 if $SiO_2$ is used instead of C for the layer 646. A thicker layer 646 (e.g., about 5 nm to about 20 nm) may enable more efficient undercutting of the layer 646 underneath the electrode 616. The resultant suspended electrode 616 may facilitate actuation of the electrode 616 to reduce the size of gap G between the top and bottom electrodes 616, 618 to a targeted gap G size in the range of about 0.3 nm to about 2 nm, and more particularly about 1 nm or less.

FIGS. 7O-7P illustrate further steps of a nanochannel formation, including depositing materials to bury or enclose the trenches 630, 632. In one example, an additional layer of material 650 is deposited on top of the layer 615 and into the trenches 630, 632. The material of layer 650 that is positioned within the trenches 630, 632 may define side walls of the nanochannel 614 to help retain the fluid and DNA strands passing through the nanochannel 614. Portions of the layer 650 positioned within trenches 630, 632 may be deposited directly onto the top surface of the substrate 612 and/or the bottom or second electrode 618.

FIG. 7P illustrates a top view of the arrangement shown in FIG. 7O. In at least some examples, the layer 650 may be formed using sputter deposition. Even with the layer 650 deposited as shown in FIG. 7O, the top electrode 616 may be suspended and movable vertically toward and away from the bottom electrode 618.

FIGS. 7Q and 7R illustrate a further step of forming the DNA sequencing device and the resulting device 600 in FIG. 7R. FIG. 7Q shows formation of fluid reservoirs on opposite ends of the nanochannel 614. FIG. 7R shows electrical contacts 656 formed for contact with the top electrode 616. In one example, the reservoirs are formed by creating windows through the layers 650, 615, 646 in order to connect to the nanochannel 614. The electrical contacts 656 may be formed as patterning electrophoretic contacts. A further step may include opening windows through the layers 615, 646, 650 to provide access to the contacts 644 of the bottom electrode 618, as shown in FIG. 7R. Additional fabrication steps may be employed to further refine the device 600 for use in DNA sequencing methods.

Figure 8:
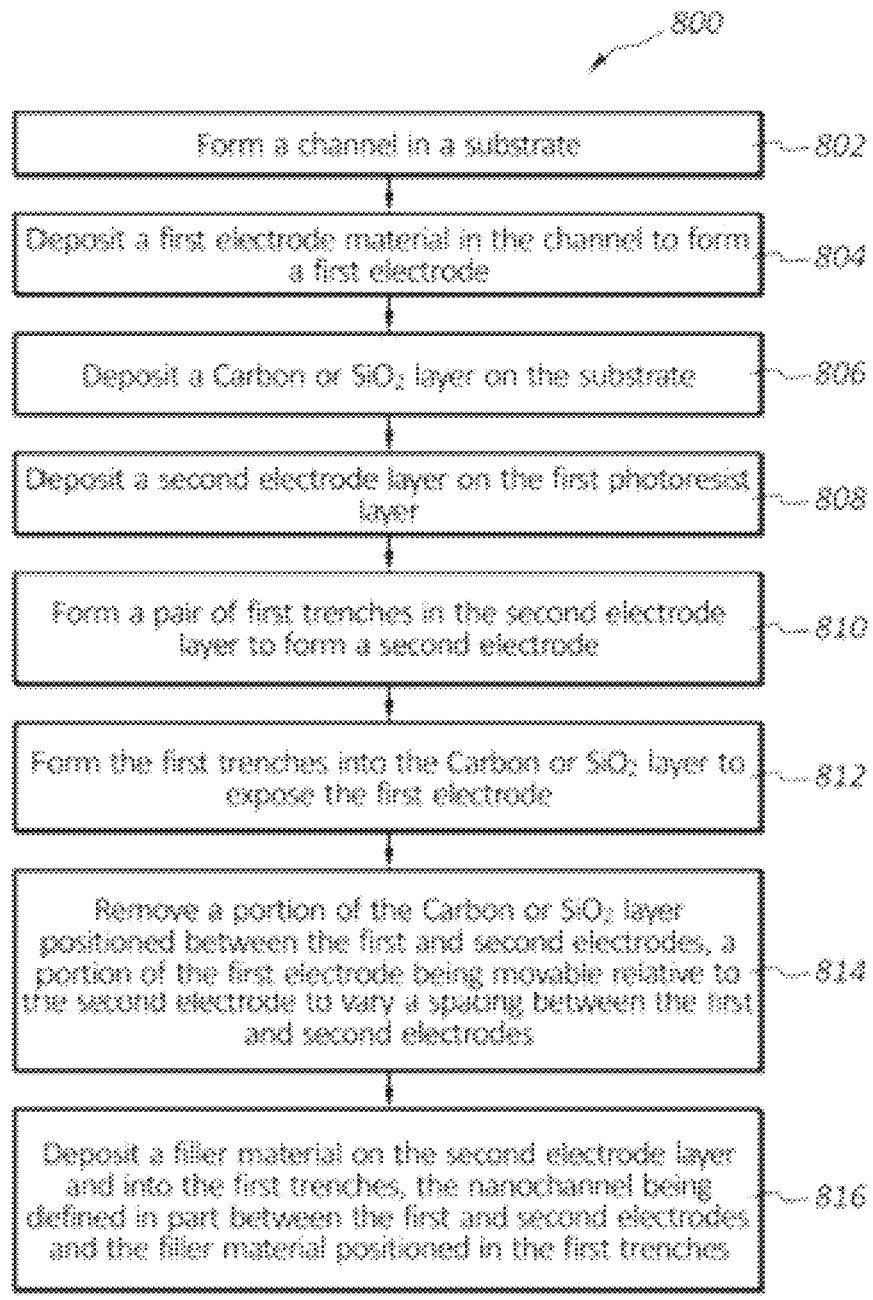
FIG. 8 is a flow diagram of an example method in accordance with the present disclosure.

Referring now to FIG. 8, an example method 800 of forming a DNA sequencing device is shown as a flow diagram. Method 800 may include, at block 802, forming a channel in a substrate. Block 804 may include depositing a first electrode material in a channel to form a first electrode. Block 806 may include depositing a carbon or SiO$_2$ layer on the substrate. Block 808 may include depositing a second electrode layer on the carbon or SiO$_2$ layer. Block 810 may include forming a pair of first trenches in the second electrode layer to form a second electrode. Block 812 may include forming the first trenches into the carbon or SiO$_2$ layer to expose the first electrode. A further step may include removing a portion of the carbon or SiO$_2$ layer positioned between the first and second electrodes, wherein a portion of the first electrode is movable relative to the second electrode to vary a spacing between the first and second electrodes at a block 814. Block 816 may include depositing a filler material on the second electrode layer and into the first trenches, wherein the nanochannel is defined in part between the first and second electrodes and the filler material positioned in the first trenches.

Method 800 may also include forming the first trenches in the second electrode layer by trench patterning using at least one of deep ultraviolet (DUV) lithography, 193 nm lithography, E-Beam lithography, and nano-imprint lithography (NIL). Method 800 may include providing the filler material as at least one of a polymer material and an insulation material. The method 800 may include, prior to forming the channel in the substrate, the steps of coating the substrate to form a first layer, and forming a trench in the first layer, followed by etching the channel in the substrate through the trench, and stripping the first layer from the insulator substrate after depositing the first electrode material in the channel and before depositing the carbon or SiO$_2$ layer on the substrate. The method 800 may also include, before forming the first trenches in the second electrode layer, the steps of forming a photoresist layer on the second electrode layer, and forming the first trenches in the photoresist layer.

The method 800 may include forming the photoresist layer on the second electrode layer using spinning materials. The method 800 may include forming the first trenches in the photoresist layer by electron beam lithography to remove portions of the photoresist layer. Forming the first trenches in the carbon or SiO$_2$ layer (e.g., also referred to as a nanochannel layer) and removing the portion of the carbon or SiO$_2$ layer may include using high pressure O$_2$ reactive ion etching (RIE) or wet etching. The spacing between the first and second electrodes may be adjustable in the range of about 0.3 nm to about 2 nm.

Figure 9:
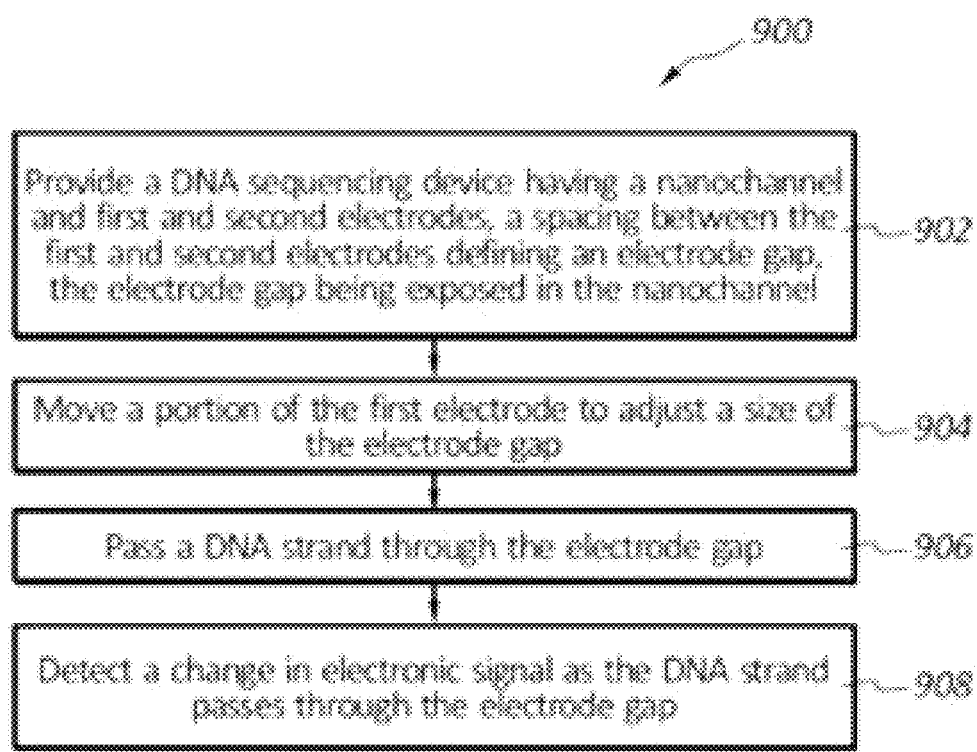
FIG. 9 is a flow diagram of another example method in accordance with the present disclosure.

FIG. 9 illustrates another example method 900 related to DNA sequencing using, for example, any of the DNA sequencing devices disclosed herein. The method 900 may include, at block 902, providing a DNA sequencing device having a nanochannel and first and second electrodes, wherein a spacing between the first and second electrodes defines an electrode gap, and the electrode gap is exposed in a nanochannel. At block 904, the method may include moving a portion of the first electrode to adjust a size of the electrode gap. Block 906 may include passing a DNA strand through the electrode gap. Block 908 may include detecting a change in an electrical signal as the DNA strand passes through the electrode gap. The method 900 may also include providing the electrode gap with a size that is adjusted to be in the range of about 0.3 nm to about 2 nm. The electrode gap may be variable. The detected change in electronic signal may be associated with one or more individual nucleotides of the DNA strand. The change in electronic signal may be used to determine a sequence of the nucleotides for the DNA strand.

The example methods 800, 900 may, in other embodiments, include fewer or additional steps that those illustrated in FIGS. 8 and 9. Further, many other methods and method steps may be possible based on the disclosures provided herein.

Figure 10:
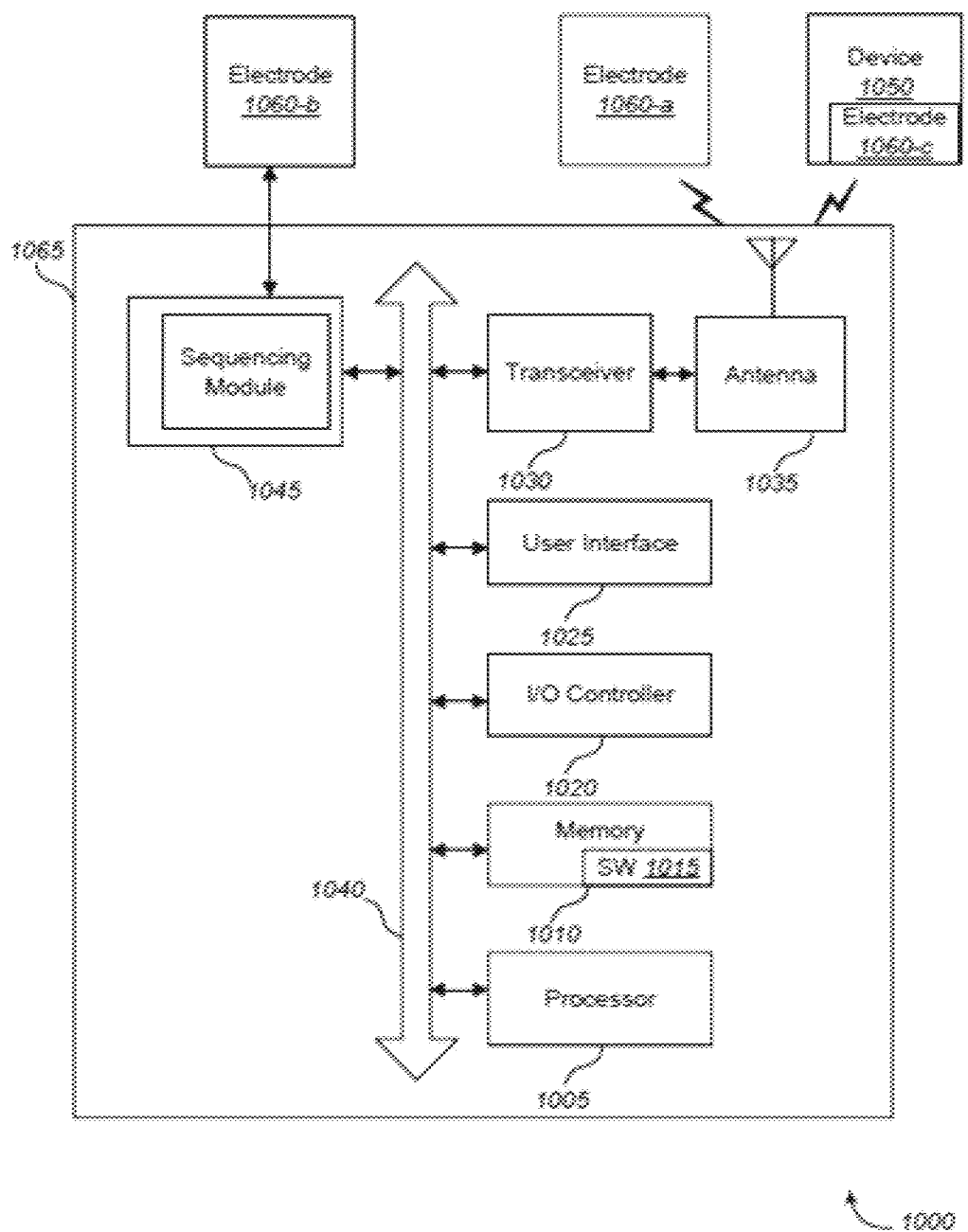
FIG. 10 is a diagram of a system in accordance with various aspects of this disclosure.

FIG. 10 shows a system 1000 for use with the DNA sequencing devices and methods shown in FIGS. 1-7 and discussed above. System 1000 may include a control panel 1065. Control panel 1065 may be equivalent at least in part to a controller, control unit, processor or the like for use with the devices described above. Control panel 1065 may include sequencing module 1045. The sequencing module 1045 may provide communications with one or more electrodes 1060-a, 1060-b, 1060-c (also referred to as sensors or devices) directly or via other communication components, such as a transceiver 1030 and/or antenna 1035. The electrodes 1060 may represent one or more of the electrodes 16, 18, or pairs of such electrodes in any of the embodiments described above. The sequencing module 1045 may perform or control various operations associated with, for example, the electrodes 16, 18, actuator 20, controller 22, or other components of the DNA sequencing devices and related methods as described above.

Control panel 1065 may also include a processor module 1005, and memory 1010 (including software/firmware code (SW) 1015), an input/output controller module 1020, a user interface module 1025, a transceiver module 1030, and one or more antennas 1035 each of which may communicate, directly or indirectly, with one another (e.g., via one or more buses 1040). The transceiver module 1030 may communicate bi-directionally, via the one or more antennas 1035, wired links, and/or wireless links, with one or more networks or remote devices. For example, the transceiver module 1030 may communicate bi-directionally with one or more of device 1050 and/or electrodes 1060-a, 1060-c. The device 1050 may be components of the DNA sequencing devices and related systems and methods described with reference to FIGS. 1-7, or other devices in communication with such systems and devices. The transceiver 1030 may include a modem to modulate the packets and provide the modulated packets to the one or more antennas 1035 for transmission, and to demodulate packets received from the one or more antennas 1035. In some embodiments (not shown) the transceiver may be communicate bi-directionally with one or more of device 1050, remote control device (not shown), and/or electrodes 1060-*a*, 1060-*c* through a hardwired connection without necessarily using antenna 1035. While a control panel or a control device (e.g., 1065) may include a single antenna 1035, the control panel or the control device may also have multiple antennas 1035 capable of concurrently transmitting or receiving multiple wired and/or wireless transmissions. In some embodiments, one element of control panel 1065 (e.g., one or more antennas 1035, transceiver module 1030, etc.) may provide a connection using wireless techniques, including digital cellular telephone connection, Cellular Digital Packet Data (CDPD) connection, digital satellite data connection, and/or another connection.

The signals associated with system 1000 may include wireless communication signals such as radio frequency, electromagnetics, local area network (LAN), wide area network (WAN), virtual private network (VPN), wireless network (using 802.11, for example), 345 MHz, Z-WAVE® communication protocol, cellular network (using 3G and/or LTE, for example), and/or other signals. The one or more antennas 1035 and/or transceiver module 1030 may include or be related to, but are not limited to, WWAN (GSM, CDMA, and WCDMA), WLAN (including BLUETOOTH® connectivity standard and Wi-Fi), WMAN (WiMAX), antennas for mobile communications, antennas for Wireless Personal Area Network (WPAN) applications (including RFID and UWB). In some embodiments, each antenna 1035 may receive signals or information specific and/or exclusive to itself. In other embodiments, each antenna 1035 may receive signals or information not specific or exclusive to itself.

In some embodiments, one or more electrodes 1060 (e.g., voltage, inductance, resistance, current, force, temperature, etc.) or devices 1050 may connect to some element of system 1000 via a network using one or more wired and/or wireless connections. In some embodiments, the user interface module 1025 may include an audio device, such as an external speaker system, an external display device such as a display screen, and/or an input device (e.g., remote control device interfaced with the user interface module 1025 directly and/or through I/O controller module 1020).

One or more buses 1040 may allow data communication between one or more elements of control panel 1065 (e.g., processor module 1005, memory 1010, I/O controller module 1020, user interface module 1025, etc.).

The memory 1010 may include random access memory (RAM), read only memory (ROM), flash RAM, and/or other types. The memory 1010 may store computer-readable, computer-executable software/firmware code 1015 including instructions that, when executed, cause the processor module 1005 to perform various functions described in this disclosure (e.g., initiating an adjustment of a lighting system, etc.). Alternatively, the software/firmware code 1015 may not be directly executable by the processor module 1005 but may cause a computer (e.g., when compiled and executed) to perform functions described herein. Alternatively, the computer-readable, computer-executable software/firmware code 1015 may not be directly executable by the processor module 1005 but may be configured to cause a computer (e.g., when compiled and executed) to perform functions described herein. The processor module 1005 may include an intelligent hardware device, e.g., a central processing unit (CPU), a microcontroller, an application-specific integrated circuit (ASIC), etc.

In some embodiments, the memory 1010 can contain, among other things, the Basic Input-Output system (BIOS) which may control basic hardware and/or software operation such as the interaction with peripheral components or devices. For example, the sequencing module 1045, and other modules and operational components of the control panel 1065 used to implement the present systems and methods may be stored within the system memory 1010. Applications resident with system 1000 are generally stored on and accessed via a non-transitory computer readable medium, such as a hard disk drive or other storage medium. Additionally, applications can be in the form of electronic signals modulated in accordance with the application and data communication technology when accessed via a network interface (e.g., transceiver module 1030, one or more antennas 1035, etc.).

Many other devices and/or subsystems may be connected to one or may be included as one or more elements of system 1000. In some embodiments, all of the elements shown in FIG. 10 need not be present to practice the present systems and methods. The devices and subsystems can be interconnected in different ways from that shown in FIG. 10. In some embodiments, an aspect of some operation of a system, such as that shown in FIG. 10, may be readily known in the art and are not discussed in detail in this application. Code to implement the present disclosure can be stored in a non-transitory computer-readable medium such as one or more of system memory 1010 or other memory. The operating system provided on I/O controller module 1020 may be iOS®, ANDROID®, MS-DOS®, MS-WINDOWS®, OS/2®, UNIX®, LINUX®, or another known operating system.

The transceiver module 1030 may include a modem configured to modulate the packets and provide the modulated packets to the antennas 1035 for transmission and/or to demodulate packets received from the antennas 1035. While the control panel or control device (e.g., 1065) may include a single antenna 1035, the control panel or control device (e.g., 1065) may have multiple antennas 1035 capable of concurrently transmitting and/or receiving multiple wireless transmissions.

In some embodiments, the DNA sequencing device and systems described herein may be used to collect electronic signals associated with the nucleotides of a DNA strand passing through the gap between electrode pairs, and the collected electronic signals are processed at a different location. The processing may include electronically comparing the collected electronic signals to ranges of electronic signals associated with specific nucleotide types which have been previously determined and stored. In other embodiments, the DNA sequencing device includes capability of processing the collected electronic signals, conducting such comparison evaluations, and even formulating an order or sequence for the nucleotides of the DNA strand being evaluated.

The detailed description set forth above in connection with the appended drawings describes examples and does not represent the only instances that may be implemented or that are within the scope of the claims. The terms "example" and "exemplary," when used in this description, mean "serving as an example, instance, or illustration," and not "preferred" or "advantageous over other examples." The detailed description includes specific details for the purpose of providing an understanding of the described techniques. These techniques, however, may be practiced without these specific details. In some instances, known structures and apparatuses are shown in block diagram form in order to avoid obscuring the concepts of the described examples.

In addition, any disclosure of components contained within other components or separate from other components should be considered exemplary because multiple other architectures may potentially be implemented to achieve the same functionality, including incorporating all, most, and/or some elements as part of one or more unitary structures and/or separate structures.

The previous description of the disclosure is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not to be limited to the examples and designs described herein but is to be accorded the broadest scope consistent with the principles and novel features disclosed.

The process parameters, actions, and steps described and/or illustrated in this disclosure are given by way of example only and can be varied as desired. For example, while the steps illustrated and/or described may be shown or discussed in a particular order, these steps do not necessarily need to be performed in the order illustrated or discussed. The various exemplary methods described and/or illustrated here may also omit one or more of the steps described or illustrated here or include additional steps in addition to those disclosed.

This description, for purposes of explanation, has been described with reference to specific embodiments. The illustrative discussions above, however, are not intended to be exhaustive or limit the present systems and methods to the precise forms discussed. Many modifications and variations are possible in view of the above teachings. The embodiments were chosen and described in order to explain the principles of the present systems and methods and their practical applications, to enable others skilled in the art to utilize the present systems, apparatus, and methods and various embodiments with various modifications as may be suited to the particular use contemplated.

What is claimed is:

1. A method of forming a nanochannel device for DNA sequencing, the method comprising:
    forming a channel in a substrate;
    depositing a first electrode material in the channel to form a first electrode;
    depositing a carbon or $SiO_2$ layer on the substrate;
    depositing a second electrode material on the carbon or $SiO_2$ layer;
    forming a pair of first trenches in the second electrode material to form a second electrode;
    continuing to form the first trenches into the carbon or $SiO_2$ layer to expose the first electrode;
    removing a portion of the carbon or $SiO_2$ layer positioned between the first and second electrodes to provide a spacing between the first and second electrodes; and
    depositing a filler material on the second electrode material and into the first trenches, with a nanochannel being defined in part between the first and second electrodes and the filler material positioned in the first trenches.

2. The method of claim 1, wherein forming the first trenches in the second electrode material includes trench patterning using at least one of deep ultraviolet (DUV) lithography, 193 nm lithography, e-beam lithography, and nanoimprint lithography (NIL).

3. The method of claim 1, wherein the filler material is at least one of a photoresist material and an insulation material.

4. The method of claim 1, further comprising:
    prior to forming the channel in the substrate:
        coating the substrate to form a first layer;
        forming a trench in the first layer; and
        etching the channel in the substrate through the trench; and
    stripping the first layer from the substrate after depositing the first electrode material in the channel and before depositing the carbon or $SiO_2$ on the substrate.

5. The method of claim 4, further comprising depositing the first electrode material on the first layer when depositing the first electrode material in the channel.

6. The method of claim 1, further comprising:
    before forming the first trenches in the second electrode material:
        forming a third photoresist layer on the second electrode material;
        forming the first trenches in the third photoresist layer.

7. The method of claim 6, wherein forming the third photoresist layer includes spinning material of the third photoresist layer on the second electrode material.

8. The method of claim 1, wherein continuing to form the first trenches in the carbon or $SiO_2$ layer and removing the portion of the carbon or $SiO_2$ layer includes using high pressure $O_2$ reactive ion etching (RIE) or wet etching.

9. The method of claim 1, wherein the spacing between the first and second electrodes is adjustable to be in the range of about 0.3 nm to about 2 nm.

* * * * *